United States Patent
Mueller-Walz

(10) Patent No.: US 9,895,327 B2
(45) Date of Patent: Feb. 20, 2018

(54) AEROSOL FORMULATIONS COMPRISING FORMOTEROL FUMARATE DIHYDRATE

(71) Applicant: Jagotec AG, Muttenz (CH)

(72) Inventor: Rudi Mueller-Walz, Schopfheim (DE)

(73) Assignee: Jagotec AG, Muttenz (CH)

( * ) Notice: Subject to any disclaimer, the term of this patent is extended or adjusted under 35 U.S.C. 154(b) by 0 days.

(21) Appl. No.: 14/953,883

(22) Filed: Nov. 30, 2015

(65) Prior Publication Data

US 2016/0310452 A1 Oct. 27, 2016

Related U.S. Application Data

(63) Continuation of application No. 13/974,570, filed on Aug. 23, 2013, now abandoned, which is a continuation of application No. 10/574,334, filed as application No. PCT/IB2004/003482 on Oct. 8, 2004, now abandoned.

(30) Foreign Application Priority Data

Oct. 9, 2003 (GB) .................................. 0323684.1

(51) Int. Cl.

| | |
|---|---|
| *A61K 8/00* | (2006.01) |
| *A61K 31/167* | (2006.01) |
| *A61K 9/00* | (2006.01) |
| *A61K 31/165* | (2006.01) |
| *A61K 31/56* | (2006.01) |
| *A61K 9/12* | (2006.01) |
| *A61M 11/04* | (2006.01) |
| *A61M 15/00* | (2006.01) |
| *A61M 16/20* | (2006.01) |

(52) U.S. Cl.
CPC ............ *A61K 31/167* (2013.01); *A61K 9/008* (2013.01); *A61K 9/12* (2013.01); *A61K 9/124* (2013.01); *A61K 31/165* (2013.01); *A61K 31/56* (2013.01); *A61M 11/04* (2013.01); *A61M 15/009* (2013.01); *A61M 16/20* (2013.01)

(58) Field of Classification Search
USPC ......................................................... 424/47
See application file for complete search history.

(56) References Cited

U.S. PATENT DOCUMENTS

| | | |
|---|---|---|
| 4,347,671 A | 9/1982 | Dias et al. |
| 5,476,603 A | 12/1995 | Buchwald et al. |
| 5,637,620 A | 6/1997 | Trofast et al. |
| 5,676,931 A | 10/1997 | Adjei et al. |
| 5,709,884 A | 1/1998 | Trofast et al. |
| 5,874,063 A | 2/1999 | Briggner et al. |
| 6,054,488 A | 4/2000 | Oliver et al. |
| 6,086,376 A | 7/2000 | Moussa et al. |
| 6,451,285 B2 | 9/2002 | Blondino et al. |
| 6,455,028 B1 | 9/2002 | Wulffhart et al. |
| 6,461,591 B1 | 10/2002 | Keller et al. |
| 6,475,467 B1 | 11/2002 | Keller et al. |
| 6,585,958 B1 | 7/2003 | Keller et al. |
| 2002/0018753 A1 | 2/2002 | Blondino et al. |
| 2002/0025299 A1 | 2/2002 | Lewis et al. |
| 2002/0099023 A1 | 7/2002 | Boucher |
| 2002/0102294 A1 | 8/2002 | Bosch et al. |
| 2002/0103260 A1 | 8/2002 | Clarke et al. |
| 2003/0114428 A1 | 6/2003 | Sequeira et al. |
| 2003/0223939 A1 | 12/2003 | Kordikowski et al. |
| 2004/0101483 A1 | 5/2004 | Muller-Walz et al. |
| 2004/0198708 A1 | 10/2004 | Kaplan et al. |
| 2005/0152846 A1 | 7/2005 | Davies et al. |
| 2006/0257324 A1 | 11/2006 | Lewis et al. |
| 2007/0218011 A1 | 9/2007 | Mueller-Walz |
| 2007/0256685 A1 | 11/2007 | Mueller-Walz |
| 2012/0263766 A1 | 10/2012 | Mueller-Walz et al. |
| 2012/0282189 A1 | 11/2012 | Mueller-Walz et al. |
| 2014/0004052 A1 | 1/2014 | Mueller-Walz |

FOREIGN PATENT DOCUMENTS

| | | |
|---|---|---|
| DE | 2503962 A1 | 8/1976 |
| EP | 0478456 A1 | 4/1992 |
| EP | 1325765 A1 | 7/2003 |
| GB | 2029441 A | 3/1980 |
| JP | 55361 B1 | 1/1980 |
| JP | 6135815 A | 5/1994 |
| JP | 9077605 A | 3/1997 |
| WO | WO-9218110 A1 | 10/1992 |
| WO | WO-9505805 A1 | 3/1995 |
| WO | WO-9515151 A1 | 6/1995 |
| WO | WO-9833479 A1 | 8/1998 |
| WO | WO-9834595 A1 | 8/1998 |

(Continued)

OTHER PUBLICATIONS

"1, 1, 1,2,3,3,3-Heptafluoropropane." *Wikipedia*. Web. Jul. 19, 2013. http://en.wikipedia.org/wiki/1, 1, 1,2,3,3,3-Heptafluoropropane.
"Cromolyn Sodium." *PubChem*. Web. Jul. 19, 2013. http://pubchem.ncbi.nlm.nih.gov/summary/summary.cgi?cid=2882.
"Formoterol Fumarate Dihydrate." *Pharmeuropa*. 14.4(2002):693-696.
Bowen et al. "Particle Size Distribution Measurement from Millimeters to Nanometers and from Rods to Platelets." *J. Disp. Sci. Technol.* 23.5(2002):631-662.
Crowder et al. "2001: An Odyssey in Inhaler Formulation and Design." *Pharm. Technol.* 25(2001):99-113.

(Continued)

*Primary Examiner* — Devang Thakor
(74) *Attorney, Agent, or Firm* — Mintz Levin Cohn Ferris Glovsky and Popeo, PC; Muriel Liberto, Esq.

(57) ABSTRACT

The invention provides a method of producing a highly stable pharmaceutical aerosol suspension formulation suitable for use in a metered dose inhaler, the formulation comprising formoterol fumarate di-hydrate in suspension, a steroid in suspension, a propellant and ethanol, the method comprising the steps of drying the formoterol fumarate di-hydrate to a water content of 4.8 to 4.28%.

18 Claims, No Drawings

(56) References Cited

FOREIGN PATENT DOCUMENTS

| | | |
|---|---|---|
| WO | WO-9851825 A1 | 11/1998 |
| WO | WO-0006121 A1 | 2/2000 |
| WO | WO-0007567 A1 | 2/2000 |
| WO | WO-0028979 A1 | 5/2000 |
| WO | WO-0047203 A1 | 8/2000 |
| WO | WO-0048587 A1 | 8/2000 |
| WO | WO-0189491 A1 | 11/2001 |
| WO | WO-0189492 A1 | 11/2001 |
| WO | WO-0207672 A2 | 1/2002 |
| WO | WO-0230394 A2 | 4/2002 |
| WO | WO-02078671 A1 | 10/2002 |
| WO | WO-03074024 A1 | 9/2003 |
| WO | WO-03086349 A1 | 10/2003 |
| WO | WO-04019985 A1 | 3/2004 |
| WO | WO-05004927 A2 | 1/2005 |
| WO | WO-05027878 A1 | 3/2005 |
| WO | WO-05034927 A2 | 4/2005 |
| WO | WO-07121913 A2 | 11/2007 |
| WO | WO-11045429 A1 | 4/2011 |
| WO | WO-11045432 A1 | 4/2011 |

OTHER PUBLICATIONS

Postma et al. "Treatment of Asthma by the Inhaled Corticosteroid Ciclesonide Given Either in the Morning or Evening." *Eur. Respir. J.* 17.6(2001):1083-1088.

AEROSOL FORMULATIONS COMPRISING FORMOTEROL FUMARATE DIHYDRATE

The present invention relates to aerosol formulations comprising formoterol fumarate di-hydrate in suspension which formulations are capable of being dispensed from a metered dose inhaler device with good delivered dose uniformity and high fine particle fraction. In particular, the invention relates to such formulations additionally comprising a steroid in suspension. The invention also relates to a method of producing such formulations.

Metered dose inhaler (MDI) formulations are well known in the art. They typically consist of suspensions or solutions of en active substance in a propellant or mixture of propellants, and contain other optional ingredients such as solvents and surfactants and preservatives. MDI formulations are stored in suitable pressurized containers that are equipped with a valve to permit an active substance to be dispensed on demand. In common with all drug products, they are subject to regulatory review as to their safety and efficacy before they can be marketed for use in humans. However, unlike oral or injectable products, which typically contain a single dosage form, an aerosol formulation for use in an MDI may contain multiple doses, e.g. tens or oven hundreds of doses in a single container, and each of these must be delivered with a uniform delivered dose, and reliable particle size uniformity. Furthermore, MDI formulations must be capable of delivering doses uniformly even after long storage periods, e.g. 2 to 3 years, under harsh conditions of temperature and humidity in order to mimic all manner of patient-use conditions.

Formoterol fumarate di-hydrate has proven to be a particularly recalcitrant material to Formulate. When formulated as suspended particles in aerosol formulations, the particles are prone to agglomeration, and to form sediments which are not readily re-dispersible. Furthermore, the particles often adhere to the inner surface of both canisters and valves. As a result, such formulations often display irregular dosing.

U.S. Pat. No. 6,054,488 addresses formulations containing formoterol fumarate as the sole active substance in suspension aerosol formulations in MDIs. This reference describes difficulties in formulating formoterol, in particular the problem of deposition of the suspended particles on canisters and valves leading to poor dose reproducibility. Often, surface active agents or other adjuvants need to be added to such formulations to counteract these problems. However, because most acceptable propellants are poor solvents for these surfactants and other adjuvants, one needs to use polar co-solvents to assist in their dissolution. Various polar co-solvents have been employed, but ethanol is a particularly useful co-solvent in this regard. However, as stated in U.S. Pat. No. 6,054,488 formulations containing an HFA and ethanol are extremely sensitive to the amount of ethanol employed. In particular, it is known that ethanol can affect the density of propellants, which can in turn alter the ability of the drug substance to be suspended. This may create complications, if one wishes to formulate additional active substances in suspension, because an appropriate ethanol level for formoterol may not be an appropriate level for suspending the other actives.

EP1152753 ('753) discloses inhalable formulations containing a combination of formoterol and the steroid—fluticasone. However, this document merely teaches the desirability of a fixed combination of the active substances in all manner of orally or nasally inhalable formulations, from nebulisers to dry powder formulations to aerosol formulations containing the active agents in suspension or solution. There is no mention of the difficulties in formulating formoterol fumarate and consequently no technical teaching as to how one should formulate this drug in combination with a steroid in an MDT formulation as an aerosol suspension, to produce a product that is capable of being delivered with a uniform delivered dose and high fine particle fraction. '753 states that ethanol can be employed in amounts of "up to 30% by weight". However, having regard to the teaching of U.S. Pat. No. 6,054,488, the disclosure of this range provides no technical teaching of workable levels of ethanol. In fact, of the 216 examples provided, only one example refers to a MIDI formulation, and it uses 2.5% by weight of ethanol.

It conspicuous that despite the disclosure of EP1152753, and despite the clearly articulated advantages in the art of a fixed combination in either dry-powder or aerosol form, and despite the fact that physicians have co-prescribed these active substances for several years before the priority date of this document, at the present time, applicant is not aware of any commercial MDI formulations containing formoterol fumarate di-hydrate in combination with fluticasone propionate.

There remains a need to provide means of stabilizing suspension formulations containing formoterol fumarate di-hydrate, particularly such formulations that additionally contain a steroid in suspension.

The applicant has now found alternative means of stabilising suspension aerosol formulations containing formoterol fumarate di-hydrate, such that it is possible to formulate highly stable aerosol formulations containing this active substance, even in combination with a steroid in suspension, without the need to adjust ethanol levels outside those effective for stabilizing a formoterol suspension formulation as a sole active agent. This is achieved by carrying out a drying step on the formoterol fumarate di-hydrate, thereby presenting it in a form with a particularly low water content, before mixing it together with other ingredients to form the formulation.

Accordingly, the invention provides in a first aspect a pharmaceutical aerosol formulation for use in a metered dose inhaler (MDI) comprising formoterol fumarate di-hydrate in suspension, a propellant and ethanol, wherein the formoterol fumarate di-hydrate is provided as suspended particles having a water content of about 4.8 to 4.28%, more particularly 4.50 to 4.28% by weight.

The present invention represents a considerable simplification in the formulation of formoterol fumarate di-hydrate, and permits of its combination in suspension with a number of steroids. The applicant has shown that such formulations can deliver the active substances with good delivered dose uniformity and high fine particle fraction.

The invention provides in a second aspect a pharmaceutical aerosol formulation for use in a metered dose inhaler (MDI) comprising formoterol fumarate di-hydrate in suspension, and a steroid in suspension, a propellant and ethanol, wherein the formoterol fumarate di-hydrate is provided as suspended particles having a water content of about 4.8 to 4.28%, more particularly 4.50 to 4.28% by weight.

Formulations according to the present invention can be filled into canisters to form highly stable suspensions for use in MDI devices. Formulations exhibit substantially no particle growth or change of morphology of the suspended particles. There is also no, or substantially no, problem of deposition of the suspended particles on the surface of either canisters or valves, and so the formulations can be discharged from a suitable MDI device with high Delivered dose uniformity.

Formulations of the present invention meet Compendial requirements as to Delivered dose uniformity as set forth, for example in the United States and European Pharmacopoeae. For example, formulations of the present invention meet the requirement set out in the USP26-NF21 chapter <601> "Delivered dose Uniformity". Indeed, the formulations appear to be so stable that they may even meet the relatively more stringent Delivered dose uniformity requirements set forth in the current Draft Guidance from the FDA, published by the CDER in October 1998.

Accordingly, the invention provides in a third aspect a pharmaceutical aerosol suspension formulation for use in a metered dose inhaler (MDI) comprising formoterol fumarate di-hydrate in suspension, and optionally a steroid in suspension, a propellant and ethanol, wherein the formoterol fumarate di-hydrate is provided as suspended particles having a water content of about 4.8 to 4.28%, more particularly 4.50 to 4.28% by weight, and wherein the formulation is capable of being dispensed from an MDI to provide a Delivered dose of formoterol fumarate di-hydrate that has a variance of no more than +/−25%, of the mean Delivered dose when the formulation is stored at, 25 degrees centigrade and 60 relative humidity (rh), more particularly 40 degrees centigrade and 75% it for up to 6 months, e.g. 1, 3 and 6 months.

Still further, the Delivered dose of the formulations contains a high fraction of fine particles, i.e. particles that are capable of penetrating the deep lung, e.g. having a diameter of less than about 5.8, more preferably less than about 4.7 microns.

Accordingly, in a fourth aspect, the invention provides a pharmaceutical aerosol suspension formulation for use in a metered dose inhaler WI) comprising formoterol fumarate di-hydrate in suspension, and optionally a steroid in suspension, a propellant and ethanol, wherein the formoterol fumarate di-hydrate has a water content of about 4.8 to 4.28%, more particularly 4.50 to 4.28% by weight, and wherein the formulation is capable of being dispensed from a MDI to provide a Delivered dose of formoterol fumarate di-hydrate with a fine particle fraction of about 30 to 70%.

When a steroid is present in a formulation according to the invention, applicant has found that the Delivered dose of steroid also meets with Compendial requirements, and the Draft FDA Guidance referred to above.

Thus, the invention provides in a fifth aspect a pharmaceutical aerosol suspension formulation for use in a metered dose inhaler (MDI) comprising formoterol fumarate di-hydrate in suspension, and a steroid in suspension, a propellant and ethanol, wherein the formoterol fumarate di-hydrate is provided as particles having a water content of about 4.8 to 4.28%, more particularly 4.50 to 4.28% by weight, suspended in the propellant and ethanol, and wherein the formulation is capable of being dispensed from a MDI to provide an Delivered dose of the steroid that has a variance of no more than +/−25%, of the mean Delivered dose when the formulation is stored at, 25 degrees centigrade and 60% rh, more particularly 40 degrees centigrade and 75% rh for up to 6 months, e.g. 1, 3 and 6 months.

In a sixth aspect of the invention there is provided a pharmaceutical aerosol suspension formulation for use in a metered dose inhaler (MDI) comprising formoterol fumarate di-hydrate in suspension, and a steroid in suspension, a propellant and ethanol, wherein the formoterol fumarate di-hydrate has a water content of about 4.8 to 4.28%, more particularly 4.5 to 4.28% by weight, wherein the formulation is capable of being dispensed from a MDI to provide an Delivered dose of steroid containing a fine particle fraction of about 30 to 70%.

Formulations of the present invention may be made by a process, which forms a seventh aspect of the invention, and comprises the step of drying the formoterol fumarate di-hydrate to a water content of about 4.8 to 4.28%, more particularly 4.50 to 4.28% by weight, before mixing the active ingredients with propellant and ethanol in a container according to techniques generally known in the art.

Formoterol fumarate di-hydrate raw material typically contains a certain amount of water in addition to the water of crystallization. Typically, the raw material is used directly in formulations. However, applicant found that by subjecting the raw material to a drying step that is designed to drive off all, or substantially all, of the residual water but not the water of crystallisation, formulations of very high stability can be achieved. Applicant found that drying to a water content of about 4.8 to 4.28%, more particularly 4.5 to 428% enabled the preparation of suspension formulations with good stability. The drying step is carried out under conditions of pressure and temperature to achieve the desired water content within a time that is both practical and economical. The skilled person will appreciate that the inventive concept resides in the realization that the material should be subjected to a drying step, to achieve the above stated preferred level of dryness, and not in the means or conditions by which the drying is achieved. Accordingly, consistent with the economic consideration, and the need to dry in a reasonably practical period of time, and consistent with the requirement of preserving the integrity of the active substance's water of crystallization, virtually any conditions of temperature and pressure earl be employed.

Preferably however, the material can be dried at a temperature of between 10 and 70° C. Preferably, also, the material can be dried at a pressure of 10 to 400 mbar.

Water content is measured according to the Karl Fischer Method. The Karl Fischer method is a well known analytical tool for the measurement, specifically, of a sample's water content. It is a titrimetric method that involves the reaction between water contained in a sample and a Karl Fischer Reagent, which is a mixture of sulphur dioxide, iodine, pyridine and methanol. The preferred reagent is Hydranal Composite 1 or 5, wherein 1 is preferred. The reagent reacts with suspended and dissolved water, Furthermore, because the sample is dissolved during this method, it is also measures water of crystallization of a sample.

The Delivered dose of a formulation is the amount of active agent to achieve a therapeutic effect or prophylactic effect that is emitted from a MDI device upon actuation. Depending on the drug substance to be emitted, and the nature of the valve, the Delivered dose may be the amount of active material emitted upon a single actuation of the MDI, or it may be the amount emitted from two or more actuations. It is not a measure of the total amount of material (actives and excipients) that is emitted upon actuation. This is often referred to as the Shot Weight.

Whilst every precaution is taken to keep formulations dry, due to residual moisture from excipients and moisture ingress that might occur during conditions of storage and use, formulations of the present invention may contain small amounts of moisture. Preferably formulations of the present invention contain levels of moisture of 50 ppm to 800 ppm, more particularly 100 to 600 pm.

The Delivered dose may not only vary between different formulations of a batch; it may also vary within a given formulation when that formulation contains a plurality, e.g. 10 or even 100 or more doses of the active substance. Accordingly, the variance of the Delivered dose is typically measured for a formulation in a given container by taking measurements at the beginning, middle and end of that formulation's life. In this way, a measure of the in-use variability in the dosing is obtained. Further, batches of formulations may be tested to obtain a picture of the inter-batch variability of a formulation after determined periods of storage. The variance of formulations according to the present invention is discussed further in the Examples. Variance, in both cases, must fall within limits set by regulatory authorities if a product is to gain market authorisation. As stated herein above, formulations of the present invention fall within all the Compendial requirements for variance of Delivered dose, and can even meet the more stringent requirements referred to in the FDA Draft Guidance for Industry published in October 1998.

The fraction of active agent contained in the total Delivered dose that is of small enough aerodynamic diameter to reach the deep lung upon inhalation is often mimed to as the fine particle fraction (or FPF) of the Delivered dose, and the absolute amount of fine particles emitted is often referred to as the Fine Particle Dose (or FPD). As stated herein above, formulations of the present invention are capable of being delivered with good Delivered dose uniformity and with a high FPF, both in relation to the formoterol fumarate di-hydrate, and the steroid.

The Delivered dose and its variance can be measured using the Dosage Unit Sampling Apparatus (DUSA). The FPF can be measured using an Andersen Cascade Impactor (ACI). The measurement methodology and the apparatus therefor are well known in the art, and are described in the United States Pharmacopoeia Chapter <601>, or in the inhalants monograph of the European Pharmacopoeia, both of which documents are hereby incorporated by reference. The USP states that the Apparatus I should be used for the measurement of FPF. The USP also states that Delivered dose Uniformity should be measured with DUSA or its equivalent. However, the Delivered dose and Delivered dose uniformity are preferably measured using the so-called Funnel Method. The Funnel Method is described in *Drug Delivery to the Lungs, VIII* p 116 to 119, which is hereby incorporated by reference. In summary, the Funnel Method consists of discharging a formulation from a MDI into a Funnel Apparatus, which basically consists of a standard Buchner Funnel. The discharged dose is captured on the glass sinter of the Funnel, and can be washed off, and the dose determined using HPLC analysis. The Funnel Method gives comparable results to the standard USP apparatus, and is generally considered to be an equivalent of the DUSA apparatus.

Formoterol fumarate di-hydrate is a long acting, selective B-2-adrenoceptor agonist. It is well known in the literature and is the active substance in the commercially available product—Foradil (registered trademark). The skilled person will be fully apprised of its properties and uses, and no further discussion needs to be had here.

Formulations of the present invention may contain from 0.001 to 0.1%, more particularly 0.003 to 0.05%, still more particularly 0.005 to 0.02% by weight of formoterol fumarate di-hydrate.

Formoterol fumarate di-hydrate is a very potent material. The typical therapeutic or prophylactic dose of this material to be emitted from an MDT device will depend upon the patient, and the type and severity of the condition to be treated. The dose may vary from about 3 to 15 micro-grams, more particularly 6 to 12 micro-grams, e.g. 10 micrograms. In a finished form, a formulation will be packaged, and will be accompanied by labeling. The dose presented on the packaging and/or labeling of a finished form is often referred to as its Label Claim. In order to ensure inter-batch quality and reproducibility, the mean dose of formulation emitted from a MDI, should not vary considerably from the Label Claim. In this regard, given the good stability of the formulation of the present invention, the mean Delivered dose of formoterol fumarate di-hydrate does not fall outside a range of +/−15% of the Label Claim.

Steroids for use in the present invention include any of the materials selected from the group consisting of budesonide, ciclesonide, mometasone, fluticasone, beclomethasone, flunisolide, loteprednol, triamcinolone, amiloride, rofleponide or a pharmaceutically acceptable salt or derivative of these active compounds, such as mometasone furoate, fluticasone dipropionate, beclomethasone dipropionate, triamcinolone acetonide or flunisolide acetate, where optically active, these materials can be used in the form of their active isomer or as an isomer mixture.

A particularly preferred steroid for use in the present invention is fluticasone propionate.

An appropriate therapeutic or prophylactic Delivered dose for the steroids will depend upon the steroid selected, the patient and the type and severity of the condition to be treated. It may vary within a range of about 10 to 2000, more particularly 100 to 1600 micro-grams daily dose.

Taking fluticasone as an example, this material is typically administered in 50, 125 and 250 micro-grams per puff (two puffs per dose). The recommended daily dose is 1000 micro-grams per day.

In respect of the steroid, the mean Delivered dose of formulations of the present invention does not fall outside a range of +/−15% of the Label Claim of the steroid.

In a preferred embodiment of the present invention, a formulation as herein above defined additionally contains a cromone selected from the group consisting of a pharmaceutically acceptable salt of cromoglycinic acid, e.g. disodium cromoglycate and/or nedocromil. Both of these materials are pharmaceutically active substances, and so their use in the present invention is limited to sub-therapeutic or sub-prophylactic levels, e.g. from about 5 to 250 micrograms per puff of a MDI inhaler. The materials may be employed to afford the formulations protection against moisture. The use of these materials to protect moisture sensitive active substances is reported in U.S. Pat. No. 6,475,467.

Preferably, formulations of the present invention contain from 0.001 to 1%, more particularly 0.005 to 0.2%, still more particularly 0.01 to 0.1% by weight cromone, e.g. disodium cromoglycate.

Suitable propellants for use in the aerosol formulations according to the invention may be any of the pressure-liquefied propellants which customarily may find use in metered-dose aerosols, for example fluorochlorocarbons such as trichloro-monofluoromethane (F11), dichlorodifluoromethane (F12), monochlorotrifluoromethane (F13), dichloro-monofluoromethane (F21), monochlorodifluoromethane (F22), monochloromonofluoromethane (P31), 1,1,2-trichloro-1,2,2-trifluoroethane (F113), 1,2-dichloro-1,1,2,2-tetrafluoroethane (F114), 1-chloro-1,1,2,2,2-pentafluoroethane (F115), 2,2-dichloro-1,1,1-trifluoroethane (F123), 1,2-dichloro-1,1,2-trifluoroethane (F123a), 2-chloro-1,1,1,2-tetrafluoroethane (F124), 2-chloro-1,1,2,2-tetrafluoroethane (F124a), 1,2-dichloro-1,1-difluoroethane (F132b), 1-chloro-1,22-trifluoroethane (F133), 2-chloro-1,1,1-trifluoroethane (F133a), 1,1-dichloro-1-fluoroethane (F141b) and 1-chloro-1,1-difluoroethane (F142b), alkanes such as propane, butane and isobutane, fluorinated alkanes such as octafluoropropane (F218) and in particular hydrofluoroalkanes such as difluoromethane (HFA 32), pentafluoroethane (HFA 125), 1,1,2,2-tetrafluoroethane (HFA 134), 1,1,1,2-tetrafluoroethane (HFA 134a), 1,1,2-trifluoroethane (HFA 143), 1,1,1-trifluoroethane (HFA 143a), difluoroethane (HFA 152a), 1,1,1,2,3,3,3-heptafluoropropane (HFA 227) and the like.

Preferred propellants are the hydrofluoroalkanes of the general formula, $$C_xH_yF_z \quad (I)$$

in which x is the number 1, 2 or 3, y and z are each an integer>=1 and y+z=2x+2.

Those hydrofluoroalkanes of the formula I in which x is the number 2 or 3 are particularly suitable.

Particularly preferred aerosol formulations are those which contain HFA 134 or HFA 227 or mixtures of these two propellants. HFA 134a and HFA 227 have a vapor pressure of about 6 bar and about 42 bar respectively at 20 [deg.] C. Both propellants differ with respect to their density (about 1.2 g/ml for HFA 134a and about 1.4 g/ml for HFA 227), which is important insofar as it is possible by suitable choice of the propellant or propellant mixture to match its density better to the density of the suspended substances and thus to keep the latter better in suspension. If desired, the density of the propellant can be further reduced by addition of cosolvents or other propellants, such as ethanol, diethyl ether, propane, n-butane or isobutane.

The aerosol formulations according to the invention cart preferably contain one or more hydrofluoroalkanes of the formula I, particularly preferably 1,1,1,2-tetrafluoroethane (HFA 134a) and/or 1,1,1,2,3,3,3-heptafluoropropane (HFA 227), and their proportion in the total formulation can preferably be at least about 50% by weight and particularly preferably at least about 80% by weight. As a rule, it is advantageous to employ these propellants in an amount of 90% by weight or more.

Ethanol is employed in the present invention in anhydrous form. It is preferred to use ethanol in as low a concentration as possible. In particular, it is preferred to use it in amounts of less than 2.5% by weight to about 1% by weight, e.g. 1 to 1.5% by weight, more particularly 1 to about 1.45% by weight.

In a particular embodiment of the invention, when using fluticasone propionate in combination with formoterol fumarate di-hydrate, it is preferred to use ethanol in an amount of 1.5% or less, e.g. 1 to 1.5% by weight.

The aerosol formulations according to the invention can contain no, or substantially no surfactant, i.e. contain less than approximately 0.0001% by weight of surface-active agents. This is particularly the case if one employs a cromone as described above. If desired, however, the formulations can contain surface-active agents conventionally employed hi aerosol formulations, such as oleic acid, lecithin, sorbitan trioleate, cetylpyridinium chloride, benzalkonium chloride, polyoxyethylene (20) sorbitan monolaurate polyoxyethylene (20) sorbitan monostearate, polyoxyethylene (20) sorbitan monooleate, polyoxypropylene/polyoxyethylene block copolymers, polyoxypropylene/polyoxyethylene/ethylenediamine block copolymers, ethoxylated castor oil and the like, where the proportion of surface-active agents, if present, can preferably be about 0.0001 to 1% by weight, in particular about 0.001 to 0.1% by weight, based on the total formulation.

Other optional adjuvants can be employed in formulations according to the present Invention. For example, if desired, they can contain buffer substances or stabilizers such as citric acid, ascorbic acid, sodium EDTA, vitamin E, N-acetylcysteine and the like. In general, such substances, if present, are used in amounts of not more than approximately 1% by weight, for example in an amount of from approximately 0.0001 to 1% by weight, based on the total formulation.

Formulations according to the present invention are prepared by a process comprising a first step of drying formoterol fumarate di-hydrate raw material to a water content as described above. If a cromone is to be employed in the formulation, preferably it too is subjected to a similar drying step. After drying, these components can be weighed and mixed with a steroid in an aerosol vial.

A valve can then be crimped onto the vial, and a pre-mix of propellant and ethanol can be introduced through the valve under pressure. The whole mixture can then be placed in an ultra-sonic bath to form a suspension of formoterol fumarate di-hydrate, and optionally the steroid.

The vials may be filled with sufficient formulation to provide a plurality of dosages. Typically formulations may contain 50 to 150 dosages, more particularly 100 to 150 dosages. The formulations are typically filled with an overage of doses to avoid a situation where a patient could, under the proper conditions of use, actuate its MDI and find that there are no remaining doses to be delivered.

The vials or canisters used to contain the formulations according to the invention may be of plastics, metal or glass construction. It is a feature of the stability of the formoterol suspension of the inventive formulations that they exhibit no, or substantially no, tendency to deposit on the surface of the containers into which they are filled. This gives the formulator the latitude to choose from any of the commercially available alternatives, which can be advantageous from an economic view point. It is often the case with suspension aerosol formulations that special containers must be used in order to avoid stability problems, for example, those coated internally with special low surface energy coating materials, see for example U.S. Pat. No. 6,596,260.

Valves used with vials may by any of the standard metered dose valves available in the art. Typically, metered dose valves of 20 to 150 micro-liters can be employed. Often the Delivered dose of one or more active substance cannot be achieved with a single actuation of an MDI. It is preferred that, having regard to the active ingredients that are contained in the formulation, and having regard to the respective Label Claims, one chooses a valve that is capable of metering the dose within only one or two actuations, or puffs.

Formulations of the present invention find use as medicinal aerosol preparations for the treatment of disease states of the lung, for example asthma, e.g. mild, exercise-induced, moderate and severe bronchial-induced asthmas, cold air-induced asthma, COPD, and interstitial lung disease sarcoidosis.

In an embodiment of the present invention, formulations are provided containing a plurality of doses of fomoterol fumarate di-hydrate, each dose containing 3 to 15 micro-grams, and a plurality of doses of fluticasone each dose containing 250 to 1000 micro-grams. Said formulations are suitable for the treatment of any of the aforementioned conditions.

Preferred features of the second and subsequent aspects of the invention are as for the first aspect mutatis mutandis.

There now follows as series of examples that serve to illustrate the invention.

EXAMPLE 1

The following formulation was prepared (FF denotes formoterol fumarate di-hydrate; FP represents fluticasone propionate; and DSCG represents disodium cromoglycate).

|             | % by weight |
|-------------|-------------|
| FF          | 0.009       |
| FP          | 0.179       |
| Abs. Ethanol| 1.429       |
| HFA 227     | 98.350      |
| DSCG        | 0.034       |

Formoterol Fumarate Di-hydrate is dried at 20 to 40° C. and at a maximum of 100 mbar reduced air pressure.

DSCG is dried at 80° C. and a maximum 100 mbar to a water content of less than 4%.

The dried materials are deposited along with the fluticasone propionate in a filling vessel and the vessel is evacuated to less than 100 mbar air pressure.

Absolute ethanol (anhydrous) and pharmaceutical grade HFA 227 are pre-blended in another container. The blending container is then connected to the filling vessel and the blend is fed into the vessel. The resultant filled vessel is homogenised for 30 minutes at 300 rpm.

A 14 mm plain aluminium container (Presspart Manufacturing, Blackburn, England), is crimped around a 50 microliter valve (Valois Pharm SA, France).

An aliquot from the filling vessel is pressure-filled into the aluminium can in a quantity sufficient for a one month medication. Filled aluminium cans formed in this fashion are weight-checked and allowed to rest for an equilibration period before testing.

EXAMPLE 2

(Measurement of Particle Size Distribution and Fine Particle Fraction)

The formulations employed are those formed according to Example 1 above,

The aerodynamic particle size distribution is determined using an Andersen Scale Impactor (ACI) fitted with the universal induction port (as set forth in the USP) at 28.3 L/minute.

20 shots (equivalent to 10 doses) of a formulation formed according to Example 1, are discharged into the ACI. Fractions of the dose are deposited at different stages of the ACI, in accordance with the particle size of the fraction. Each fraction is washed from the stage and analysed using HPLC.

HPLC analysis showed that the fine particle fraction of the dose delivered to the ACI apparatus is greater than 50% both for the formoterol fumarate di-hydrate and the fluticasone propionate.

EXAMPLE 3

Formulations of Example 1 are tested for Delivered dose Uniformity according to the following method.

Canisters containing formulations are stored at 40° C. and 75% rh for 6 months.

After the appropriate storage period, MDI devices containing formulations of Example 1 are connected with the Funnel Apparatus described herein above.

3 doses (6 shots) are discharged into the apparatus at the beginning of the life of the container; 4 doses (8 shots) are discharged in the middle life of the container; and 3 doses (6 shots) are discharged at the end of the container life. The intermediate doses/shots are discharged to waste. The delivered dose is collected by washing the glass scinter, and the dose is analysed by HPLC.

Analysis shows that after the storage period, variance of the delivered dose does not exceed +/−25% of the mean delivered dose, +/−20% of the mean delivered dose.

EXAMPLE 4

Formulations of Example 1 are tested for Delivered dose Uniformity according to the following method.

Canisters containing formulations are stored at 40° C. and 75% rh for 1, 3 and 6 months.

After the appropriate storage period, MDI devices containing formulations of Example 1 are connected with the Funnel Apparatus described herein above.

For each container, 1 dose (two shots) are discharged into the Funnel Apparatus. This is repeated for 10 containers. After washing the Funnel Apparatus and analysing using HPLC, results show that no delivered dose varies by more than +/−25% of the mean delivered dose, and more particularly +/−20% of the mean delivered dose.

The invention claimed is:

1. A method of producing a highly stable pharmaceutical aerosol suspension formulation comprising formoterol fumarate di-hydrate in suspension, a steroid in suspension, a propellant and ethanol, the method comprising the steps of
   drying a formoterol fumarate di-hydrate raw material to a water content of 4.8 to 4.28% at a temperature between 10 and 70 Celsius and a pressure of 10 to 400 mbar,
   determining the water content of the dried formoterol fumarate,
   mixing the dried formoterol fumarate di-hydrate with a steroid,
   introducing a pre-mix of propellant and ethanol, and
   forming a suspension of the formoterol fumarate di-hydrate and the steroid in the propellant and ethanol, and filling the suspension into the vial under pressure through the valve,
   such that when the formulation is dispensed from a metered dose inhaler (MDI) it provides a Delivered dose of formoterol fumarate di-hydrate that has a variance of no more than +/−25% of the mean Delivered dose when the formulation is stored at 40° C. and 75% relative humidity for up to 6 months.

2. The method of claim 1, wherein the steroid is selected from the group consisting of budesonide, ciclesonide, mometasone, fluticasone, beclomethasone, flunisolide, loteprednol, triamcinolone, amiloride, rofleponide or a pharmaceutically acceptable salt or derivative of these active compounds, selected from mometasone furoate, fluticasone propionate, beclomethasone dipropionate, triamcinolone acetonide and flunisolide acetate.

3. The method of claim 2, wherein the steroid is fluticasone propionate.

4. The method of claim 3, wherein the fluticasone propionate is present in an amount of 0.05 to 2% by weight of the formulation.

5. The method of claim 1, wherein the formoterol fumarate di-hydrate is present in an amount of 0.001 to 0.1% by weight of the formulation.

6. The method of claim 1, further comprising a step of drying a cromone selected from the group consisting of a pharmaceutically acceptable salt of cromoglycinic acid, nedocromil, and mixtures thereof, and mixing the cromone with the dried formoterol fumarate di-hydrate and the steroid.

7. The method of claim 6, wherein the cromone is present in the formulation in an amount of 0.001 to 1%.

8. The method of claim 1, wherein the propellant is a hydrofluoroalkane of the general formula: $C_xH_yF_z$ in which x is the number 1, 2 or 3, y and z are each an integer greater than or equal to ($\geq$) 1, and y+z=2x+2.

9. The method of claim 8, wherein the propellant is HFA 134a or HFA 227 or a mixture thereof.

10. The method of claim 1, wherein the propellant is employed in an amount of greater than 90% by weight.

11. The method of claim 1, wherein the ethanol is present in amounts of less than 2.5% by weight.

12. The method of claim 1, wherein the vial is in the form of an aluminum, uncoated container.

13. The method of claim 12, wherein the vial is adapted to be placed in a metered dose inhaler and each dose of the plurality of doses contains 3 to 15 micrograms of formoterol fumarate di-hydrate.

14. The method of claim 13, wherein each dose of the plurality of doses contains 50 to 500 micrograms of fluticasone proprionate.

15. The method of claim 1, wherein the mixing step is performed prior to introducing the dried formoterol fumarate di-hydrate and steroid into an aerosol vial.

16. The method of claim 1, wherein the dried formoterol fumarate di-hydrate and steroid are mixed in an aerosol vial.

17. The method of claim 15 or 16 wherein the amount of dried formoterol fumarate di-hydrate and steroid is sufficient to provide a plurality of dosages.

18. The method of claim 15, 16, or 17, wherein the vial comprises or is adapted to comprise a metered dose valve.

* * * * *

UNITED STATES PATENT AND TRADEMARK OFFICE
CERTIFICATE OF CORRECTION

PATENT NO. : 9,895,327 B2
APPLICATION NO. : 14/953883
DATED : February 20, 2018
INVENTOR(S) : Rudi Mueller-Walz It is certified that error appears in the above-identified patent and that said Letters Patent is hereby corrected as shown below:

On the Title Page

Item (63) – Related U.S. Application Data: - please correct the application No. from "PCT/IB2004/003482" to -- PCT/IB2004/003481 --.

Signed and Sealed this
Twentieth Day of November, 2018

Andrei Iancu
*Director of the United States Patent and Trademark Office*